United States Patent
Stern et al.

(10) Patent No.: US 10,926,060 B2
(45) Date of Patent: Feb. 23, 2021

(54) FLEXIBLE TIP CATHETER

(71) Applicant: Covidien LP, Mansfield, MA (US)

(72) Inventors: George Stern, Irvine, CA (US); Edwin Bon, Lake Elsinore, CA (US); Edwin Wang, Tustin, CA (US); Ujwal Jalgaonkar, Irvine, CA (US); Peter Skujins, Laguna Hills, CA (US)

(73) Assignee: Covidien LP, Mansfield, MA (US)

( * ) Notice: Subject to any disclaimer, the term of this patent is extended or adjusted under 35 U.S.C. 154(b) by 601 days.

(21) Appl. No.: 15/448,028

(22) Filed: Mar. 2, 2017

(65) Prior Publication Data
US 2018/0250498 A1 Sep. 6, 2018

(51) Int. Cl.
*A61M 25/00* (2006.01)
*A61M 25/01* (2006.01)
*A61B 17/22* (2006.01)

(52) U.S. Cl.
CPC ... *A61M 25/0068* (2013.01); *A61B 17/22031* (2013.01); *A61M 25/001* (2013.01); *A61M 25/008* (2013.01); *A61M 25/0012* (2013.01); *A61M 25/0045* (2013.01); *A61M 25/0052* (2013.01); *A61M 25/0054* (2013.01); *A61M 25/0097* (2013.01); *A61M 25/0108* (2013.01); *A61B 2017/22035* (2013.01); *A61B 2017/22079* (2013.01); *A61M 2205/0222* (2013.01)

(58) Field of Classification Search
CPC .......... A61M 25/0068; A61M 25/0045; A61M 25/0012; A61M 25/005; A61M 25/0054; A61M 25/008
See application file for complete search history.

(56) References Cited

U.S. PATENT DOCUMENTS

| | | |
|---|---|---|
| 4,354,491 A | 10/1982 | Marbry |
| 4,405,314 A | 9/1983 | Cope |
| 4,739,768 A | 4/1988 | Engelson |
| 4,763,671 A | 8/1988 | Goffinet |
| 4,930,521 A | 6/1990 | Metzger et al. |
| 4,976,690 A | 12/1990 | Solar et al. |
| 5,007,901 A | 4/1991 | Shields |

(Continued)

FOREIGN PATENT DOCUMENTS

| | | |
|---|---|---|
| EP | 0643979 A1 | 8/1994 |
| EP | 0810003 A2 | 12/1997 |

(Continued)

OTHER PUBLICATIONS

"Engage™ Polyolefin Elastomers," Product Selection Guide, Dow®, published Aug. 2015, 4 pp.

(Continued)

*Primary Examiner* — Kami A Bosworth
*Assistant Examiner* — Leah J Swanson
(74) *Attorney, Agent, or Firm* — Shumaker & Sieffert, P.A.

(57) ABSTRACT

In some examples, a catheter includes an elongated body comprising proximal and distal portions. The distal portion of the elongated body comprises an inner liner that includes a proximal liner section and a distal liner section that include different materials, and an outer jacket positioned over the inner liner. The distal liner section has a first hardness and the proximal liner section has a second hardness, where the first hardness is less than the second hardness.

46 Claims, 3 Drawing Sheets

(56) References Cited

U.S. PATENT DOCUMENTS

| | | | |
|---|---|---|---|
| 5,308,342 A | 5/1994 | Sepetka et al. | |
| 5,331,019 A * | 7/1994 | Payne, Jr. | A61L 2/08 |
| | | | 522/157 |
| 5,380,307 A | 1/1995 | Chee et al. | |
| 5,423,776 A | 6/1995 | Haindl | |
| 5,437,632 A | 8/1995 | Engelson | |
| 5,454,795 A | 10/1995 | Samson | |
| 5,499,973 A | 3/1996 | Saab | |
| 5,531,685 A | 7/1996 | Hemmer et al. | |
| 5,649,909 A | 7/1997 | Cornelius | |
| 5,755,704 A | 5/1998 | Lunn | |
| 5,792,124 A | 8/1998 | Horrigan et al. | |
| 5,830,227 A | 11/1998 | Fischell et al. | |
| 5,833,604 A | 11/1998 | Houser et al. | |
| 5,971,975 A | 10/1999 | Mills et al. | |
| 5,984,907 A | 11/1999 | McGee et al. | |
| 6,045,547 A | 4/2000 | Ren et al. | |
| 6,143,013 A | 11/2000 | Samson et al. | |
| 6,217,565 B1 | 4/2001 | Cohen | |
| 6,302,875 B1 * | 10/2001 | Makower | A61B 8/12 |
| | | | 604/528 |
| 6,319,244 B2 | 11/2001 | Suresh et al. | |
| 6,436,112 B2 | 8/2002 | Wensel et al. | |
| 6,582,536 B2 | 6/2003 | Shimada | |
| 6,591,472 B1 | 7/2003 | Noone et al. | |
| 6,622,367 B1 | 9/2003 | Bolduc et al. | |
| 6,841,214 B1 | 1/2005 | Keith et al. | |
| 7,306,585 B2 | 12/2007 | Ross | |
| 7,527,606 B2 | 5/2009 | Oepen | |
| 7,625,337 B2 | 12/2009 | Campbell et al. | |
| 7,658,723 B2 | 2/2010 | Von Oepen et al. | |
| 8,105,246 B2 | 1/2012 | Voeller et al. | |
| 8,142,413 B2 | 3/2012 | Root et al. | |
| 8,241,245 B2 | 8/2012 | Markel et al. | |
| 8,251,976 B2 | 8/2012 | Zhou | |
| 8,282,677 B2 | 10/2012 | O'Connor et al. | |
| 8,323,432 B2 | 12/2012 | Quint | |
| 8,382,738 B2 | 2/2013 | Simpson et al. | |
| 8,574,283 B1 | 11/2013 | Kamat | |
| 8,608,754 B2 | 12/2013 | Wensel et al. | |
| 8,652,193 B2 | 2/2014 | Dorn | |
| 8,684,999 B2 | 4/2014 | Tegg et al. | |
| 8,702,679 B2 | 4/2014 | Deckman et al. | |
| 8,725,228 B2 | 5/2014 | Koblish et al. | |
| 8,758,295 B2 | 6/2014 | Schaeffer | |
| 8,911,424 B2 | 12/2014 | Weadock et al. | |
| 8,926,560 B2 | 1/2015 | Dinh et al. | |
| 9,352,116 B2 | 5/2016 | Guo et al. | |
| 2002/0156459 A1 | 10/2002 | Ye et al. | |
| 2003/0135198 A1 | 7/2003 | Berhow et al. | |
| 2004/0087933 A1 | 5/2004 | Lee et al. | |
| 2006/0264905 A1 | 11/2006 | Eskridge et al. | |
| 2008/0048011 A1 | 2/2008 | Weller | |
| 2008/0188832 A1 * | 8/2008 | Tanioka | A61M 25/0012 |
| | | | 604/525 |
| 2009/0030400 A1 | 1/2009 | Bose et al. | |
| 2010/0049192 A1 | 2/2010 | Holtz et al. | |
| 2011/0028940 A1 | 2/2011 | Lorenz | |
| 2011/0238041 A1 | 9/2011 | Lim et al. | |
| 2012/0041411 A1 | 2/2012 | Horton et al. | |
| 2012/0101480 A1 | 4/2012 | Ingle et al. | |
| 2012/0116350 A1 | 5/2012 | Strauss et al. | |
| 2012/0172717 A1 | 7/2012 | Gonda | |
| 2012/0245562 A1 | 9/2012 | Bihlmaier | |
| 2012/0303051 A1 | 11/2012 | Matsuura | |
| 2013/0172851 A1 | 7/2013 | Shimada et al. | |
| 2013/0245610 A1 | 9/2013 | Haslinger et al. | |
| 2013/0253417 A1 | 9/2013 | Dinh et al. | |
| 2014/0046297 A1 | 2/2014 | Shimada et al. | |
| 2014/0173878 A1 | 6/2014 | Merk et al. | |
| 2014/0214006 A1 * | 7/2014 | Hiroshige | A61M 25/0012 |
| | | | 604/527 |
| 2014/0243963 A1 | 8/2014 | Sheps et al. | |
| 2014/0277058 A1 | 9/2014 | Wu | |
| 2015/0100043 A1 | 4/2015 | Govari et al. | |
| 2015/0157827 A1 | 6/2015 | Glasel | |
| 2015/0216692 A1 | 8/2015 | Shannon et al. | |
| 2015/0283357 A1 * | 10/2015 | Lampropoulos | B32B 37/182 |
| | | | 604/523 |
| 2016/0346503 A1 | 12/2016 | Jackson et al. | |
| 2016/0346506 A1 | 12/2016 | Jackson et al. | |
| 2016/0346507 A1 | 12/2016 | Jackson et al. | |
| 2016/0346508 A1 | 12/2016 | Williams et al. | |

FOREIGN PATENT DOCUMENTS

| | | |
|---|---|---|
| WO | 9305842 A1 | 4/1993 |
| WO | 2003004085 A2 | 1/2003 |
| WO | 2004033015 A1 | 4/2004 |
| WO | 2007050718 A1 | 5/2007 |
| WO | 2010068793 A1 | 6/2010 |
| WO | 2013185148 A1 | 12/2013 |
| WO | 2017004194 A1 | 1/2017 |

OTHER PUBLICATIONS

"Grilamid TR, Transparent polyamide for the most exacting requirements," Grilamid TRE® EMS, Oct. 2014, 36 pp.

"Engage™ 8440 Polyolefin Elastomers," Technical Information, Dow®, published Nov. 30, 2000, revised Sep. 7, 2011, 2 pp.

"Poly Blend™ 1100 Series," Material Safety Data Sheet, manufacturer, AdvanSource Biomaterials, date prepared Jul. 22, 2008, 2 pp.

"Poly Blend™ 1100," AdvanSource Biomaterials, accessed on Nov. 16, 2016, 2 pp.

"Biotechnology Companies; Patent Application Titled "Steerable Catheter Having Intermediate Stiffness Transition Zone" Published Online," Biotech Business Week, NewsRx LLC, Sep. 22, 2014, 5 pp.

"Entellus Medical, Inc.; Patent Issued for Guide Catheter and Method of Use," Medical Devices & Surgical Technology Week, NewsRx, Mar. 16, 2014, 6 pp.

"Braid-Reinforced Shafts," Vention Medical, retrieved from http://www.ventionmedical.com/products-and-services/braid-reinforced-shafts/ on Jan. 19, 2015, 2 pp.

"Braided Catheter Shafts & Coiled Catheter Shafts," AdvancedCath, retrieved from http://advancedcathetermanufacturing.com/braided-and-coiled-catheter-shafts/ on Jan. 19, 2015, 2 pp.

"C-Flex™ Ureteral Catheters," Boston Scientific, retrieved from http://www.bostonscientific.com/en-US/products/catheters—ureteral/c-flex.html on Jan. 15, 2015, 3 pp.

"Marathon™ Flow Directed Micro Catheters," Covidien, retrieved from http://www.ev3.net/neuro/us/micro-catheters/marathontrade-flow-directed-catheter.htm on Jan. 19, 2015, 2 pp.

"Microcatheters: Valet® Microcatheter," Volcano Corporation, retrieved from http://www.volcanocorp.com/products/valet.php#.VddxLflVhvB on Jan. 15, 2015, 2 pp.

"Putnam Plastics New Taper-TIE™ Technology Optimizes Variable Flexibility of Medical Catheter Shafts," Dec. 18, 2012, 1 pp.

"Sidekick® Support Catheter, Enhanced Crosser® Catheter Deliverability," Bard Peripheral Vascular, 2013, (Applicant points out, in accordance with MPEP 609.04(a), that the year of publication, 2013, is sufficiently earlier than the effective U.S. filing date, 2017, so that the particular month of publication is not in issue.) 2 pp.

Hartford, "New Extrusion Techniques Advance Catheter Design," Medical Device and Diagnostic Industry, Feb. 20, 2013, 4 pp.

International Search Report and Written Opinion issued in International Application No. PCT/US2018/020410, dated Aug. 7, 2018, 12 pp.

International Preliminary Report on Patentability from International Application No. PCT/US2018/020410, dated Sep. 12, 2019, 8 pp.

Communication Pursuant to Rules 161(1) and 162 EPC dated Oct. 10, 2019 from counterpart European Application No. 18724347.2, 3 pp.

Response to Communication Pursuant to Rules 161(1) and 162 EPC dated Apr. 2, 2020, from counterpart European Application No. 18724347.2, 16 pp.

* cited by examiner

FLEXIBLE TIP CATHETER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, the disclosure describes example catheters that include an inner liner and an outer jacket, where a distal section of the inner liner is more flexible than a more proximal section of the inner liner. The relatively flexible distal portion of the inner liner may provide the catheter with a relatively flexible tip and improved navigability though a tortuous vasculature of a patient (e.g., better kink resistance at the tip). In some examples, the outer jacket also decreases in relative hardness moving distally toward the distal end of the catheter, which may also help improve navigability of the catheter though a tortuous vasculature of a patient. In some examples, the catheters described herein may be configured to resist geometric deformation when the distal end of the catheter body is engaged with a guidewire. This disclosure also describes example methods of forming catheters and methods of using catheters.

Clause 1: In one example, a catheter includes an elongated body that includes proximal and distal portions, the distal portion of the elongated body having an inner liner that includes a proximal liner section and a distal liner section that include different materials, and an outer jacket positioned over the inner liner. The distal liner section has a first hardness, and the proximal liner section has a second hardness, where the first hardness is less than the second hardness.

Clause 2: In some examples of the catheter of clause 1, the catheter includes a support element positioned between the inner liner and the outer jacket.

Clause 3: In some examples of the catheter of clause 2, the support element includes a braided structure including at least two strands of different diameters.

Clause 4: In some examples of the catheter of clause 3, the braided structure includes at least one flat or half-round wire and at least one round wire.

Clause 5: In some examples of the catheter of clause 4, the braided structure includes four flat or half-round wires woven against four round wires.

Clause 6: In some examples of the catheter of clause 2, the support element is embedded in at least one of the inner liner or the outer jacket.

Clause 7: In some examples of the catheter of clause 2, the support element includes at least one of a metal braid or a metal coil.

Clause 8: In some examples of the catheter of clause 1, the distal liner section includes a thermoplastic elastomer.

Clause 9: In some examples of the catheter of clause 8, the distal liner section further includes a slip agent.

Clause 10: In some examples of the catheter of clause 9, the slip agent includes an amide derived from a monosaturated fatty acid and is mixed with the polyolefin elastomer in an amount of about 0.5 weight percent (wt. %).

Clause 11: In some examples of the catheter of clause 9, the proximal liner section includes a fluoropolymer.

Clause 12: In some examples of the catheter of clause 1, the distal liner section includes a polyolefin elastomer and a slip agent, and the proximal liner section includes polytetrafluoroethylene (PTFE).

Clause 13: In some examples of the catheter of clause 1, the proximal liner section extends to a proximal end of the elongated body.

Clause 14: In some examples of the catheter of clause 1, the inner liner further includes an intermediate liner section defining a hardness less than that of the proximal liner section and greater than that of the distal liner section.

Clause 15: In some examples of the catheter of clause 14, the intermediate liner section includes a polyolefin elastomer and a slip agent.

Clause 16: In some examples of the catheter of clause 14, the intermediate liner section and the distal liner section collectively define an axial length of at least about 0.2 cm extending along a central axis of the elongated body.

Clause 17: In some examples of the catheter of clause 1, the distal liner section is less lubricious than the proximal liner section.

Clause 18: In some examples of the catheter of clause 1, the distal liner section includes a radial thickness of about 0.0015 inches (about 38 micrometers).

Clause 19: In some examples of the catheter of clause 1, the distal liner section defines a lumen having a diameter of about 0.89 mm to about 2.24 mm.

Clause 20: In some examples of the catheter of clause 1, the catheter includes a radiopaque marker band disposed over the distal liner section.

Clause 21: In some examples of the catheter of clause 1, the outer jacket includes a proximal jacket section and a distal jacket section, the proximal jacket section having a greater hardness than the distal jacket section.

Clause 22: In some examples of the catheter of clause 21, the catheter includes a plurality of intermediate jacket sections positioned between the proximal jacket section and the distal jacket section, the outer jacket defines a hardness gradient of decreasing hardness moving distally from the proximal jacket section to a distal most intermediate jacket section of the plurality of intermediate jacket sections.

Clause 23: In some examples of the catheter of clause 22, the proximal jacket section and the plurality of intermediate jacket sections together define sequential sections of different hardnesses.

Clause 24: In some examples of the catheter of clause 22, the proximal jacket section defines a Shore D hardness of about 63-85.

Clause 25: In some examples of the catheter of clause 22, the plurality of intermediate jacket sections includes at least one jacket section including a polyether block amide, at least one jacket section including a polyolefin elastomer, and at least one jacket section including a polyurethane elastomer.

Clause 26: In some examples of the catheter of clause 22, the hardness gradient region transitions from a Shore D hardness of about 72 to a Shore A hardness of about 30.

Clause 27: In some examples of the catheter of clause 26, the plurality of intermediate jacket sections includes at least four intermediate jacket sections.

Clause 28: In some examples of the catheter of clause 27, the distal most intermediate jacket section includes a polyurethane elastomer, and a proximal most intermediate jacket section includes a polyether block amide.

Clause 29: In some examples of the catheter of clause 22, the distal jacket section defines a hardness between about a Shore A hardness of 30 and about a Shore D hardness of 55.

Clause 30: In some examples of the catheter of clause 22, the proximal jacket section includes a polyamide and the distal jacket section includes a polyolefin elastomer.

Clause 31: In some examples of the catheter of clause 1, the distal portion of the elongated body defines a wall thickness of less than about 0.15 mm.

Clause 32: In some examples of the catheter of clause 1, the catheter includes a tie layer positioned between the inner liner and the outer jacket.

Clause 33: In some examples of the catheter of clause 32, the catheter includes a support element positioned over the tie layer.

Clause 34: In one example, a method of forming an elongated body of a catheter includes positioning an inner liner over a mandrel, the inner liner including a proximal liner section and a distal liner section including different materials, the distal liner section having a first hardness less than a second hardness of the proximal liner section; and positioning an outer jacket over the inner liner.

Clause 35: In some examples of the method of clause 34, the method includes forming the inner liner, wherein forming the inner liner extruding a mixture including a first polyolefin elastomer and a slip agent to form the distal liner section, and bonding the distal liner section to the proximal liner section to form the inner liner.

Clause 36: In some examples of the method of clause 34, the method includes forming the inner liner by extruding a mixture including a first polyolefin elastomer and a slip agent to form the distal liner section; extruding a mixture including a second polyolefin elastomer to form an intermediate liner section; and bonding a first end of the intermediate liner section to the proximal liner section and a second end of the intermediate liner section to the distal liner section to form the inner liner.

Clause 37: In some examples of the method of clause 34, the method includes positioning a support element over the inner liner, the support element including at least one of a wire braid or a wire coil.

Clause 38: In some examples of the method of clause 37, positioning the support element includes weaving or wrapping a plurality of metal wires over the inner liner while the inner liner is on the mandrel, the plurality of metal wires including at least two wires of different diameters.

Clause 39: In some examples of the method of clause 37, positioning the support element includes weaving four flat or half-round wires against four round wires to form the wire braid.

Clause 40: In some examples of the method of clause 37, the method includes heat setting the support element on a mandrel prior to positioning the support element over the inner liner.

Clause 41: In some examples of the method of clause 34, the method includes positioning a radiopaque marker over the distal liner section prior to positioning the outer jacket over the inner liner and the support element.

Clause 42: In some examples of the method of clause 34, positioning the outer jacket over the inner liner includes positioning a proximal jacket section over the inner liner, and positioning a plurality of intermediate jacket sections over the inner liner such that the outer jacket defines a hardness gradient of decreasing hardness moving distally from the proximal jacket section to a distal most intermediate jacket section of the plurality of intermediate jacket sections.

Clause 43: In some examples of the method of clause 42, positioning the outer jacket over the inner liner further includes positioning a distal jacket section over the inner liner such that the outer jacket includes a sequential arrangement of the proximal jacket section, the plurality of intermediate jacket sections, and the distal jacket section; and bonding contacting portions of the proximal jacket section, the plurality of intermediate jacket sections, and the distal jacket section to one another.

Clause 44: In some examples of the method of clause 43, the distal jacket section defines a hardness that is greater than that of the distal most intermediate jacket section.

Clause 45: In one example, a method for treating a thrombus within a vasculature of a patient includes inserting the catheter of clause 1 into the vasculature of the patient; and aspirating the thrombus using the catheter.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
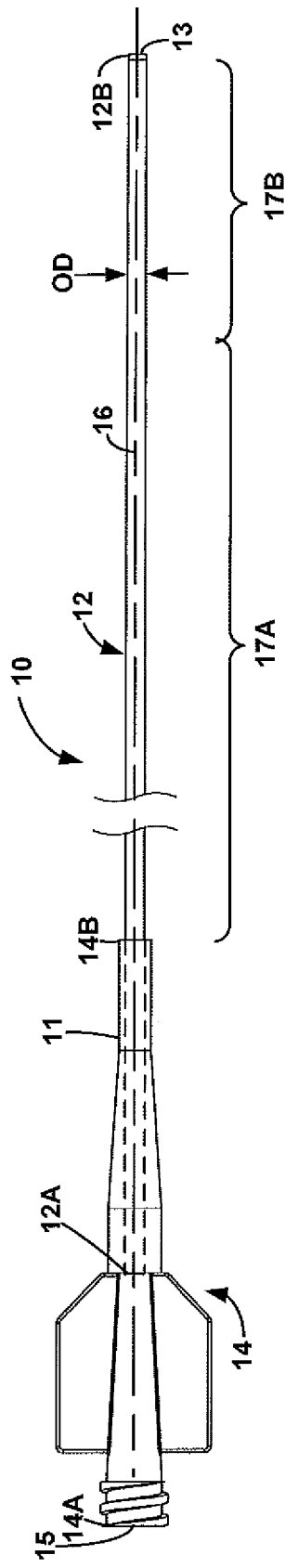
FIG. 1 is a conceptual side elevation view of an example catheter, which includes an elongated body and a hub.

In some examples, a medical catheter ("catheter") described herein includes a relatively flexible elongated body that is configured to be navigated through vasculature of a patient, e.g., tortuous vasculature in a brain of the patient. The elongated body of the catheter is configured to exhibit a relatively high level of structural integrity while defining a thin-walled construction. In this way, the catheter may maintain a relatively low profile (e.g., a relatively small outer diameter), while still providing a relatively large inner lumen (also referred to as a working channel in some examples), through which distal tissue sites may be accessed, e.g., to deliver a medical device or therapeutic agent, to remove a thrombus or other target from the patient's body, or any combination thereof.

The described catheters may include a relatively flexible distal portion that can be configured to be navigated through vasculature of a patient, e.g., tortuous vasculature in a brain of the patient, where the distal portion may exhibit increased flexibility relative to a proximal portion of the catheter. In some examples, the elongated body includes an inner liner and an outer jacket, and the increased flexibility of the distal portion may be at least partially (e.g., partially or fully) attributable to the configuration of the inner liner. For example, in some cases, a distal section of the inner liner may be more flexible than a more proximal section of the inner liner. In this way, the inner liner, as well as the catheter, may be a variable stiffness catheter that increases in flexibility towards a distal end of the catheter. For example, the inner liner may have sections of different hardnesses (e.g., sections of different materials) such that the distal-most section of the inner liner has a decreased hardness compared to a more proximal section of the inner liner. In some examples, the inner liner may include a plurality of inner liner sections that define a hardness gradient that decreases from a proximal-most section of the inner liner to a distal-most section of the inner liner.

Additionally, in some examples, the outer jacket within the distal portion of the catheter may likewise define sections of different materials and hardnesses such that a distal section of the outer jacket has a decreased hardness compared to a more proximal section of the outer jacket. In some examples, sections of "different materials" may include sections of similar polymeric constructions whose relative amounts and/or additive have been altered to result in sections of different relative hardnesses. In some examples, the outer jacket may include a plurality of intermediate jacket sections (e.g., four or more intermediate jacket sections) positioned between a proximal jacket section and a distal jacket section such that the outer jacket defines a hardness gradient that decreases from the proximal jacket section to the distal most intermediate jacket section.

The elongated body of the catheter can be configured to exhibit a relatively high level of flexibility, pushability, torqueability, and/or structural integrity. In some examples, the elongated body of the catheter includes an inner liner, a support element (e.g. metal coil or braid), and an outer jacket, which can interact to provide a relatively flexible elongated body of the catheter with sufficient structural integrity (e.g., columnar strength) to permit the elongated body of the catheter to be advanced through the vasculature via a pushing force applied to a proximal portion of the elongated body of the catheter, e.g. without buckling, kinking, or otherwise undesirably deforming (e.g., ovalization). In addition, in some examples, the elongated body of the catheter has a columnar strength and flexibility that allow at least a distal portion of the elongated body of the catheter to be navigated from a femoral artery, through the aorta of the patient, and into the intracranial vascular system of the patient, e.g., to reach a relatively distal treatment site, including the middle cerebral artery (MCA), the Circle of Willis, and tissue sites more distal than the MCA and the Circle of Willis. The MCA and, consequently, vasculature distal to the MCA may be relatively difficult to access due to the carotid siphon or vertebral artery anatomy that must be traversed to reach such locations.

In some examples, the catheter may be a guide catheter that acts as a conduit to help support a microcatheter. In other examples, the catheter may be a microcatheter. In either example, the elongated body of the catheter of the catheter may define an inner lumen, which may be configured to receive one or more medical devices, deliver a therapeutic agent to a distal tissue site, remove thrombus (e.g., by aspiration) from the patient's vasculature, and the like or any combination thereof. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots.

In examples in which the inner lumen defined by the elongated body of the catheter is used to remove thrombus from vasculature, the catheter may be referred to as an aspiration catheter. A vacuum may be applied to a proximal end of the elongated body of the catheter to draw a thrombus into the inner lumen, e.g., by a suction pump. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip configuration that is configured to substantially maintain its shape, even in the presence of the vacuum force applied to the catheter during the aspiration process.

The catheters described herein may be advanced to a target location within vasculature of the patient in cooperation with a guidewire, an inner catheter, or both, which may aid in the navigation (e.g., steering and manipulation) of the catheter through the vasculature. For example, an inner lumen of the catheter body may be configured to receive a guidewire or an inner catheter, such that the catheter body may be guided through vasculature over the guidewire or the inner catheter. As described in further detail below, in some examples, a distal tip of the catheter body is configured to resist geometric deformation from forces applied to the distal tip by the guidewire or inner catheter. This resistance to geometric deformation may help improve the ease with which the catheter body may be guided to a relatively distal tissue site, e.g., through relatively tight turns in the vasculature.

Although primarily described as being used to reach relatively distal vasculature sites, the relatively thin-walled and kink resistant catheters described herein may readily be configured to be used with other target tissue sites. For example, the catheters may be used to access tissue sites throughout the coronary and peripheral vasculature, the gastrointestinal tract, the urethra, ureters, Fallopian tubes and other body lumens.

FIG. 1 is a conceptual side view of an example catheter 10, which includes elongated body 12 and a hub 14 positioned at a proximal end 12A of elongated body 12. In some examples, catheter hub 14 may define an opening through which an inner lumen 24 (shown in FIG. 2) of elongated body 12 may be accessed and, in some examples, closed. For example, catheter hub 14 may include a luer connector for connecting to another device, a hemostasis valve, or another mechanism or combination of mechanisms for establishing connections between catheter 10 and other devices. In other examples, the proximal end of catheter 10 can include another structure in addition to or instead of hub 14.

Elongated body 12 extends from proximal end 12A to distal end 12B, and defines a proximal portion 17A and a distal portion 17B. Elongated body 12 may define at least one inner lumen 24 (shown in FIG. 2) that extends the length of elongated body 12. In the example shown in FIG. 1, proximal end 12A of elongated body 12 is received within hub 14 and can be mechanically connected to hub 14 via an adhesive, welding, or another suitable technique or combination of techniques. Opening 15 defined by hub 14 and located at proximal end 14A of hub 14 is aligned with the inner lumen 24 (shown in FIG. 2) of elongated body 12, such that the inner lumen 24 of elongated body 12 may be accessed via opening 15. In some examples, catheter 10 may include a strain relief body 11, which may be a part of hub 14 or may be separate from hub 14.

In some cases, a clinician may steer catheter 10 through the vasculature of a patient by pushing or rotating hub 14 to navigate distal portion 17B of elongated body 12 through the vasculature of a patient. The clinician may apply torque to hub 14 and/or proximal portion 17A of the catheter 10 (or at least a portion of elongated body 12 that is more proximal than distal portion 17B implanted in the patient) in order to rotate distal portion 17B of catheter 10.

As described further below, in some examples, elongated body 12 includes an inner liner, support element, and outer jacket, which may configure elongated body 12 to better transmit the torque applied to a relatively proximal portion to a relatively distal portion of elongated body 12, resist kinking or otherwise undesirable deformation upon rotation of catheter 10, and/or exhibit a high degree of responsiveness from the relatively proximal portion 17A of elongated body 12. In addition, distal portion 17B of elongated body 12 may be configured to provide increased flexibility to assist the navigation of catheter 10 through the extensive curvatures of a vasculature, which can be relatively tortuous in some anatomical regions.

In some examples, catheter 10 may be a guide catheter that acts as a conduit to help support a microcatheter. In other examples, catheter 10 may be a microcatheter. In either example, elongated body 12 of catheter 10 may define at least one inner lumen 24 (e.g., one inner lumen, two inner lumens, three inner lumens or more than three inner lumens), which may be configured to receive one or more medical devices, serve as a conduit for the delivery of a medical device, deliver a therapeutic agent to a distal tissue site, remove thrombus (e.g., by aspiration) from the patient's vasculature, and the like or any combination thereof. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots. In examples in which inner lumen 24 defined by elongated body 12 is used to remove thrombus from vasculature, catheter 10 may be referred to as an aspiration catheter. A vacuum may be applied to proximal end 12A of elongated body 12 (e.g., at opening 15) to draw a thrombus into inner lumen 24. An aspiration catheter may be used in a medical procedure to treat an ischemic insult, which may occur due to occlusion of a blood vessel that deprives brain tissue of oxygen-carrying blood. In some examples, in addition to being configured to be navigated to relatively distal tissue sites, an aspiration catheter may also include a distal tip that is configured to substantially maintain its shape, even in the presence of the vacuum force applied to the catheter during the aspiration process.

In some examples, elongated body 12 may be used to access relatively distal vasculature locations in a patient, such as the MCA in a brain of a patient. The MCA, as well as other vasculature in the brain or other relatively distal tissue sites (e.g., relative to the vasculature access point), may be relatively difficult to reach with a catheter, due at least in part to the tortuous pathway (e.g., comprising relatively sharp twists and/or turns) through the vasculature to reach these tissue sites.

Figure 2:
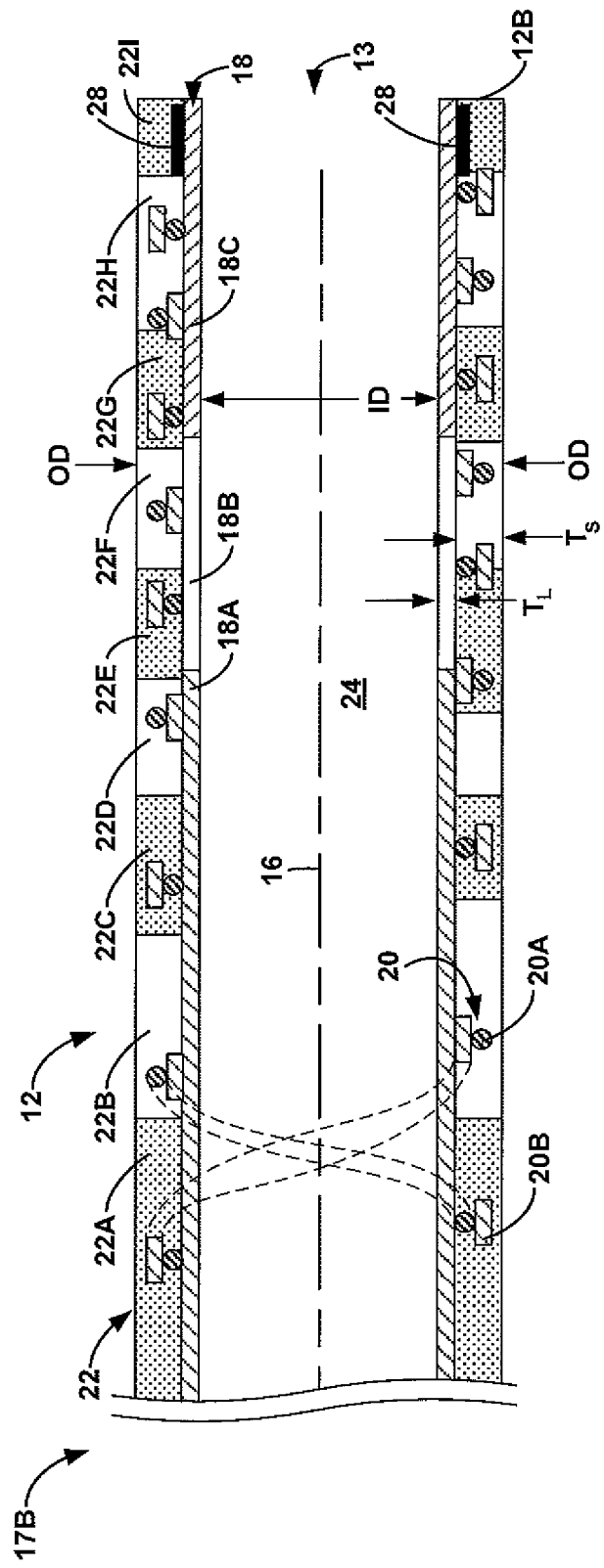
FIG. 2 is a conceptual axial cross-sectional view of the distal portion of the elongated body of FIG. 1, where the cross-section is taken through a center of the elongated body along a longitudinal axis.

Distal portion 17B of catheter 10 may be configured to be relatively flexible compared to proximal portion 17A of elongated body 12 to allow for improved navigability of elongated body 12 through a tortuous vasculature of a patient. FIG. 2 shows a conceptual axial cross-sectional view of distal portion 17B of catheter 10 of FIG. 1, where the cross-section is taken through a center of elongated body 12 along a longitudinal axis 16. As shown in FIG. 2, elongated body 12 includes an inner liner 18, a support element 20, and an outer jacket 22.

Inner liner 18 comprises a proximal section (proximal liner section 18A), an optional intermediate section (intermediate liner section 18B), and a distal section (distal liner section 18C) formed from of different materials such that distal liner section 18C has a lower hardness and higher flexibility compared to proximal liner section 18A. Reducing the hardness and increasing the flexibility of the distal liner section 18C compared to proximal liner section 18A may improve the navigability of catheter 10 without compromising or reducing the structural integrity (e.g., kink resistance) of elongated body 12. In some examples, distal portion 17B of catheter 10 may also include at least one support element 20 such as a braid or coil formed over inner liner 18 and embedded within or located beneath an outer jacket 22. Support element 20 can be formed from any suitable material, such as, but not limited to, a metal, a polymer, a fiber, or any combination thereof. As described further below, outer jacket 22 may include regions of different hardnesses such that outer jacket 22 defines a hardness gradient where the hardness of the outer jacket 22 generally decreases moving distally over distal portion 17B.

In some examples, inner liner 18 extends from proximal end 12A to distal end 12B of elongated body 12 with proximal liner section 18A extending along a substantial portion of elongated body 12 (e.g., extend to proximal end 12A). Inner liner 18 defines inner lumen 24 of elongated body 12, inner lumen 24 extending from proximal end 12A to distal end 12B and defining a passageway extending from proximal end 12A to distal opening 13 at distal end 12B of elongated body 12. Inner lumen 24 may be sized to receive a medical device (e.g., another catheter, a guidewire, an embolic protection device, a stent, a thrombectomy device, or any combination thereof), a therapeutic agent, or the like.

Inner liner 18 may be composed of different materials including, for example, one or more thermoplastic elastomers such as polyolefin elastomers, thermoplastic polyolefins, fluoropolymers such as polytetrafluoroethylene (PTFE), perfluoroalkyoxy alkane (PFA), fluorinated ethylene propylene (FEP), or the like. The different materials may include sections of similar polymeric constructions whose relative amounts and/or additive have been altered to result in sections of different relative hardnesses. In some examples, inner liner 18 can be formed as independent tubular sections that are subsequently joined together using any suitable technique, such as an adhesive, fusing/welding, or any combination thereof.

Proximal liner section 18A may include of materials that exhibit high lubricity and a Shore D hardness (ASTM D2240) of about 50-65. In some examples, proximal liner section 18A may include a non-etched PTFE, e.g., may consist essentially of a non-etched PTFE. PTFE may exhibit a relatively high lubricity, such that the inner surface of proximal liner section 18A may exhibit a relatively low friction coefficient to facilitate the introduction and passage of a medical device (e.g., another catheter, a guidewire, an embolic protection device, a stent, a thrombectomy device, or any combination thereof) through inner lumen 24. In some examples, proximal liner section 18A may include PTFE such as Teflon® PTFE 640 available from The Chemours Company, Inc. having a Shore D hardness of about 58D.

Distal liner section 18C may include of materials that exhibit lower hardness and higher flexibility compared to proximal liner section 18A to improve the navigability the catheter 10 within the vasculature of a patient. In some examples, distal liner section 18C may include a thermoplastic elastomer having a Shore D hardness of about 11 to about 47. In some examples, distal liner section 18C may include one or more polyolefins including, for example, a polyolefin elastomers such as Engage™ polyolefin elastomers available from the Dow Chemical Company of Midland, Mich. In some examples, distal liner section 18C may include polyolefin elastomer ethylene butane such as Engage™ 7270 having a Shore D hardness of about 26.

In some examples, distal liner section 18C may be positioned directly adjacent to proximal liner section 18A, thereby excluding the presence of an intermediate liner section. Alternatively, distal portion 17B may include an optional intermediate liner section 18B to provide a stepped change in hardnesses between proximal liner section 18A and distal liner section 18C. In some such examples, intermediate liner section 18B may have a Shore D hardness of about 12 to about 47. In some examples, intermediate liner section 18C may include one or more polyolefins including, for example, a polyolefin elastomer such as Engage™ 8440 having a Shore D hardness of about 36.

In some examples, the polymers used to form intermediate or distal liner sections 18B, 18C may exhibit a higher coefficient of friction compared to the harder polymers (e.g., PTFE) that form proximal liner section 18A. To improve the lubricity of the softer polymers forming intermediate or distal liner sections 18B, 18C, one or more of intermediate and distal liner sections 18B, 18C may include one or more slip agents. The one or more slip agents may help increase the lubricity of the respective liner section which can help improve the navigability of catheter 10 by facilitating the smooth passage of distal portion 17B over a guide catheter or guidewire. Suitable slip agents may include, for example, an amide derived from a monosaturated fatty acid such as Ampacet 100329 slip concentrate available from Ampacet Corporation of Tarrytown, N.Y. Ampacet 100329 is characterized as 5 weight percent (wt. %) erucamide in metallocene linear low-density polyethylene. The slip agent may be added to the polymeric materials that form intermediate or distal liner sections 18B, 18C in an amount of about 0.1 wt. % to about 1 wt. % (e.g., 1-10 wt. % of Ampacet 100329 is added to distal liner section 18C corresponding to 0.1-1 wt. % of the erucamide slip agent being added). The slip agent may be mixed and extruded along with the thermoplastic elastomer (e.g., a polyolefin elastomer ethylene butane such as, but not limited to, Engage™ 7270 or 8440) used to form intermediate or distal liner sections 18B, 18C.

Intermediate and distal liner sections 18B, 18C may be of any suitable length (e.g., distance extending along the direction of longitudinal axis 16). In some examples, the combined length of intermediate and distal liner sections 18B, 18C may be from about 5 cm centimeters (cm) to about 45 cm, such as from about 15 cm to about 30 cm. In some examples, the length of distal liner section 18C may be greater than the length of intermediate liner 18B. For example, the length of intermediate liner section 18B may be about 15 cm and the length of distal liner section 18C may be about 20 cm. In other examples, the length of distal liner section 18C may be less than the length of intermediate liner 18B. For example, the length of intermediate liner section 18B may be about 20 cm and the length of distal liner section 18C may be about 10 cm.

Elongated body 12 may include one or more support elements 20 positioned over inner liner 18. In some examples, support element 20 may include at least one braided structure, coil structure, or combinations thereof. Support element 20 may be structurally configured to be relatively flexible, pushable, navigable, and relatively kink- and buckle-resistant, so that elongated body 12 may resist buckling when a pushing force is applied to a relatively proximal portion of catheter 10 to advance elongated body 12 distally through vasculature, and so that it may resist kinking when traversing around a tight turn in the vasculature. Unwanted kinking and/or buckling of elongated body 12 may otherwise hinder a clinician's efforts to push the elongated body 12 distally, e.g., past a turn. In some examples, support element 20 may be tailored to increase the structural integrity of elongated body 12 while allowing elongated body 12 to remain relatively flexible. For example, support element 20, together with inner liner 18, and outer jacket 22, may help distribute pushing and rotational forces along a length of elongated body 12, while also providing structural support to help prevent kinking or buckling of elongated body 12 upon bending or rotation of elongated body 12. As a result, a clinician may apply pushing forces, rotational forces, or both, to a proximal portion of elongated body 12, and such forces may cause a distal portion of elongated body 12 to advance distally, rotate, or both, respectively.

In some examples, support element 20 may include a braided structure having wires or filaments of different diameters, different cross-sectional shapes, different materials, or any combination thereof. For example, as shown in FIG. 2, support element 20 may include a combination of round wires 20A and flat wires 20B. Round wires 20A may be substantially circular in cross-section and flat wires 20B may be a quadrilateral in cross-section, where the cross-sections are taking in a direction orthogonal to the longitudinal axis of the respective wire when the wire is substantially straight. The cross-sectional dimension of the wire (e.g., the diameter) can sometimes be referred to as the size of the wire. For example, a 0.0015 inch round wire 20A may have a circular cross-sectional diameter of about 0.0015 inches and a 0.001×0.008 inch flat wire 20B may have cross-sectional diameters of about 0.001 inches and about 0.008 inches.

In some examples, the braided structure may include a wire braid including round wires 20A woven against flat wires 20B, such that there is no cross braiding of the respective round wires 20A or flat wires 20B. In some such examples, support element 20 may include 0.0015 inch or 0.002 inch round wires 20A and 0.001×0.002 inch, 0.001× 0.005 inch, or 0.001×0.008 inch flat wires 20B, or combinations thereof. For example, support element 20 may include round wires 20A that have a cross-sectional diameter of about 0.0015 inches (e.g., about 38 μm) and flat wires 20B with a cross-sectional diameter of about 0.001×0.005 inches (e.g., about 25×125 μm); round wires 20A that have a cross-sectional diameter of about 0.002 inches (e.g., about 50 μm) and flat wires 20B with a cross-sectional diameter of about 0.001×0.005 inches (e.g., about 25×125 μm); round wires 20A that have a cross-sectional diameter of about 0.002 inches (e.g., about 50 μm) and flat wires 20B with a cross-sectional diameter of about 0.001×0.008 inches (e.g., about 25×200 μm); or round wires 20A that have a cross-sectional diameter of about 0.0015 inches (e.g., about 38 μm) and flat wires 20B with a cross-sectional diameter of about 0.001×0.008 inches (e.g., about 25×200 μm). In some examples the wire braid may include 8 wires (e.g., four round wires 20A woven against four flat wires 20B), 16 wires (e.g., eight round wires 20A woven against eight flat wires 20B), or the like.

In some examples, the braided combination of round wires 20A and flat wires 20B may provide elongated body 12 with better ovalization resistance and tensile strength compared to other catheter designs (e.g., a support element consisting of only one metal coil or a braid consisting of only round wires). For example, including support element 20 made of an eight-wire braid (e.g., four 0.002 inches round wires 20A woven against four 0.001×0.008 inch flat wires 20B such that the round wires 20A do not cross another round wire 20A) may provide for greater kink and ovalization resistance compared to a single coil construction of comparable thickness without adding to the thickness or the tubular wall. Additionally, the combination of round wires 20A and flat wires 20B may define a relatively thin jacket thickness ($T_S$) and/or sidewall thickness (e.g., $T_S+T_L$) while still providing a high tensile strength with kink resistance and pushability.

Though support element 20 is primarily described as a braided structure of different diameter wires, in some examples, support element 20 may comprise a wire braid of similarly sized wires (e.g. wires with similar cross-sectional sizes), round or flat filaments made of synthetic or polymeric materials (e.g., non-metal wires), or combinations thereof. For example, support element 20 may include a 16 wire braid comprising of only 0.001×0.002 inches (e.g., about 25×50 μm) flat wires.

In some examples, in addition to or instead of a braided structure, support element 20 may include one or more coil structures. The coil structures (e.g., wire coils) may exhibit columnar strength (e.g., kink resistance) and/or hoop strength (e.g., resistance to ovalization) compared to other catheter designs. The one or more coil structures forming support element 20 may each define a plurality of turns in the shape of a helical coil, each coil defining a central axis substantially aligned or coincident with longitudinal axis 16. In some examples, wherein support element 20 includes one or more coil structures, the coils may be interspaced with each other in a longitudinal direction (in a direction along longitudinal axis 16) such that the helical coils are wound in the same direction (e.g., a right-handed wind or a left-handed wind) with one turn (e.g., one full circumvolution about inner liner 18) of a respective coil is positioned between an adjacent turn of the other coil so that the turns of both coils are longitudinally offset from one another along the length of elongated body 12 and the coils do not overlap along the length of elongated body 12. In some examples, the interspaced arrangement of the more than one coil structures may allow for improved rotational responsiveness and structural integrity.

In other examples, support element 20 may include both a coil structure and braided structure (e.g., a wire braid over a wire coil or vice versa). For example, support element 20 may include an inner stainless steel wire coil made of either a round wire (e.g., 0.0015 inch round wire coil) or a flat wire (e.g., 0.001×0.002 inch, 0.001×0.005 inch, or 0.001×0.008 inch flat wires). A wire braid can be positioned over the inner wire coil (e.g., an 8 or 16 wire braid that includes 0.0005× 0.002 inch flat wires).

In some examples, support element 20 may be formed using braids or coils made of metal wires. Any suitable sized metal wire may be used to form the metal coils or metal braids. In some examples, the metal wires used to form support element 20 may have one or two cross-sectional diameters each measuring between about 0.0005 inches to about 0.008 inches (e.g., about 13 μm to about 200 μm). The metal wires may include round wires (e.g., circular cross-section), half-round wires (e.g., oval cross-section), flat wires (e.g., rectangular cross-section), or any suitable combination thereof. In some examples where support element 20 includes one or more wire coils, the coils may include round wires having a cross-sectional diameter of about 0.002 inches (e.g., about 50 μm). In some examples, support element 20 may include a braided structure that includes one or more round wires, half-round/flat wires, or combinations thereof.

In some examples, support element 20 may define a variable pitch along the length of elongated body 12. As used herein, the "pitch" is used to refer to the length along axis 16 for a single wire (e.g., a single round wire 20A) to complete one revolution around axis 16. For example, a wire coil having a pitch equal to the cross-sectional diameter of the wire means that the wire will be tightly coiled such that each loop of the wire is in continuous contact with an adjacent loop. In some examples, the pitch of support element 20 may decrease moving distally within distal portion 17B. In some examples, support element 20 may define a variable pick braid along the length of elongated body 12. As used herein, the term "pick" is used to refer to the number of overlaps or "picks" along axis 16 defining the density of the braid. For example, a braid having a high picks-per-inch value may have round wires 20A overlapping opposing flat wires 20B with increased frequency along axis 16. In some examples, the pick count of support element 20 may increase moving distally within distal portion 17B.

In some examples, support element 20 may be an etched or cut hypotube such as a spirally cut hypotube. In such examples, the hypotube may define a smaller diameter compared to inner liner 18. The hypotube may be radially expanded (e.g., partially uncoiled) to fit over the inner liner.

Suitable materials for support element 20 may include, for example, one or more metals such as nickel titanium alloy (e.g., Nitinol, tertiary Nitinols), stainless steel, tungsten, titanium, gold, platinum, palladium, tantalum, silver, or a nickel-chromium alloy, a cobalt-chromium alloy, or the like. In such examples, support element may include stainless steel wires, which may provide increased strength to elongated body 12 (e.g., to increase the resistance of elongated body 12 to kinking. In some examples, support element 20 may be selected to include a radiopaque material(s) to allow elongated body 12 to be easily observed by the clinician as catheter 10 is advanced through the vasculature of a patient. In some examples support element 20 may be cladded with one or more materials, for example, to improve the radiopacity of the element without altering the underlying structural characteristics of the base wire (e.g., Nitinol wire cladded in gold).

In some examples, support element 20 may include non-metal materials such as one or more synthetic fibers including, for example, at least one of a para-aramid material, liquid crystal polymer (LCP), poly(p-phenylene-2,6-benzobisoxazole), polyether amides, polycarbonates, PTFE, PEEK, ultra-high molecular weight polyethylene, polyethylene naphthalate, polyester, carbon fiber, a glass-fiber reinforced polymer, a carbon-fiber reinforced polymer, or the like. In some examples, support element 20 may include one or more polymers including, for example, polycarbonate, polyimide, polyetherimide, polyphenylene sulfide, polyether-ether-ketone, one or more fluoropolymers such as polytetrafluoroethylene, poly(ethene-cotetrafluoroethene), fluorinated ethylene propylene, polyvinylidene fluoride, or the like, one or more thermoplastic polymers such as polyether block amide, a polyamide, a polyamide-based polymer (e.g., nylon), a polyurethane, a polyolefin, PEBAX, polypropylene, a thermoplastic elastomer, one or more thermoset polymers, or the like. In some examples, support element 20 may include substantially hard and/or rigid based polymer materials including, for example, Kevlar, LCP, nylon, ultra-high molecular weight polyethylene, FPEN, polyester, glass-fiber reinforced or carbon-fiber reinforced polymers, or the like that may be used to provide columnar and or hoop strength to elongated body 12. In some examples, forming support element 20 using a thermoplastic polymer may help improve the flexibility of the elongated body 12. In some examples, the round wires 20A and/or flat wires 20B of support element 20 described above may be replaced with similarly sized components formed from one or more of the synthetic/polymeric materials described above.

Elongate body 12 includes outer jacket 22 positioned over support element 20 and inner liner 18, the support element 20 being positioned between inner liner 18 and outer jacket 22 in at least some portions of elongated body 12. In some examples, outer jacket 22 may include various regions of different hardnesses such that outer jacket 22 defines a hardness gradient where the hardness of the outer jacket 22 generally decreases moving distally along elongate body 12. For example, outer jacket 22 may define hardness gradient within distal portion 17B that transitions from a Shore D hardness of about 85 at a proximal section (e.g., proximal jacket section 22A) to a Shore A hardness (ASTM D2240) of about 30 at a distal section (e.g., intermediate jacket section 22H just proximal to distal jacket section 22I).

In some examples, the described hardness gradient of outer jacket 22 may be a step gradient, where the hardness changes sequentially dependent on the composition of the outer jacket within a specific section. For example, each outer jacket section (e.g., proximal jacket section 22A, one or more intermediate jacket sections 22B-22H, and distal jacket section 22I) may be formed from different materials that provide different relative hardnesses for each respective section. In some examples, the different materials may include sections of similar polymeric constructions whose relative amounts and/or additives have been altered to result in sections of different relative hardnesses.

In some examples, proximal jacket section 22A may include polymeric materials that exhibit a Shore D hardness of about 63 to 85. An example polymeric material for proximal jacket section 22A may include polyamides such as Grilamid® TR 55 (polyamide 12) (available from EMS-Grivory of Sumter, S.C.) having a Shore D hardness of about 85 or polyamides such as Grilamid® L 25 (polyamide 12) available from EMS-Grivory having a Shore D hardness of about 72.

In the example shown in FIG. 2, distal portion 17B of elongated body 12 may include one or more intermediate jacket sections 22B-22H. In some examples, intermediate jacket sections 22B-22H may include polymeric materials of decreasing hardness, such that the hardness of outer jacket 22 decreases from a Shore D hardness of about 72 within intermediate jacket section 22B to a Shore D hardness of about 26 within intermediate jacket section 22H. Example polymeric materials for intermediate jacket sections 22B-22H may include for example polyether block amide such as Pebax® commercially available from Arkema Group of Colombes, France, polyurethane elastomers such as PolyBlend 1100™ available from AdvanSource Biomaterials of St. Wilmington, Mass., polyolefin elastomers (e.g., Engage™ polyolefin elastomer available from Dow Chemical Company of Midland, Mich.), thermoplastic polyurethanes such as Pellethane® TPU available from The Lubrizol Corporation of Wickliffe, Ohio, or the like. In some examples, intermediate jacket section 22B may include a polyether block amide (e.g., Pebax® 72D) having a Shore D hardness of about 72, intermediate jacket section 22C may include a polyether block amide (e.g., Pebax® 63D) having a Shore D hardness of about 63, intermediate jacket section 22D may include a polyether block amide (e.g., Pebax® 55D) having a Shore D hardness of about 55, intermediate jacket section 22E may include a polyether block amide or a polyolefin elastomer (e.g., Pebax® 40D, Pebax® 45D, or Engage™ 8480) having a Shore D hardness of about 40-45, intermediate jacket section 22F may include a polyether block amide or a polyolefin elastomer (e.g., Pebax® 35D, or Engage™ 8440G) having a Shore D hardness of about 35-36, intermediate jacket section 22G may include a polyether block amide or a polyolefin elastomers having (e.g., Pebax® 25D or Engage™ 7270) a Shore D hardness of about 25-26, and intermediate jacket section 22H may include a polyurethane elastomer (e.g., PolyBlend 1100™) having a Shore A hardness of about 30.

In some examples, distal jacket section 22I may be configured to have a higher lubricity compared to other sections of outer jacket 22 to provide for improved navigability of elongated body 12 through a tortious vasculature of a patient relative to an elongated body that includes a distal jacket section having the same lubricity as the more proximal jacket sections. In some examples, distal jacket section 22I may have the same or lower hardness compared to distal most intermediate jacket section 22H. In such examples, the jacket hardness gradient may be characterized as extending from proximal jacket section 22A to distal jacket section 22I. In other examples, jacket section 22I may have a hardness less than that of proximal jacket section 22A, but more than the hardness of the distal most intermediate jacket section (e.g., intermediate jacket section 22H). In some examples, distal jacket section 22I may exhibit a Shore D hardness of about 26 to about 55. In some such examples the increased hardness of distal jacket section 22I may provide better support for radiopaque marker 28. Example polymeric materials for distal jacket section 22H may include for example polyolefin elastomers such as polyolefin elastomer ethylene butane (e.g., Engage™ 7270) having a Shore D hardness of about 26.

Intermediate and distal jacket sections 22B-22I may be of any suitable length (e.g., distance extending along the direction of central axis 16). In some examples, the combined length of intermediate and distal jacket sections 22B-22I may be about 10 cm to about 40 cm, in some examples about 20 cm. In some examples, each intermediate jacket section 22B may individually range in length from between about 0 cm to about 25 cm. The choice of length for the different intermediate jacket sections may be dependent in part on the location of the target treatment site within the vasculature of a patient. For example, in examples where catheter 10 must navigate particularly tortuous sections of vasculature, the relatively intermediate jacket sections may be sized such that the more flexible jacket sections are the ones passing through the corresponding tortuous confines of the vasculature. In some non-limiting examples, intermediate jacket section 22B may be about 2 to about 10 cm (e.g., about 5 cm), intermediate jacket section 22C may be about 2 cm to about 10 cm (e.g., about 8 cm), intermediate jacket section 22D may be about 0 cm to about 8 cm (e.g., about 6 cm), intermediate jacket section 22E may be about 0 cm to about 6 cm (e.g., about 1 cm), intermediate jacket section 22F may be about 0 cm to about 4 cm (e.g., about 1 cm), intermediate jacket section 22G may be about 1 cm to about 3 cm (e.g., about 1 cm), intermediate jacket section 22H may be about 4 cm to about 30 cm (e.g., about 25 cm), and distal jacket section 22I may be about 0.05 cm to about 1 cm (e.g., about 0.2 cm).

In some examples, at least a portion of an outer surface of outer jacket 22 includes one or more coatings, such as, but not limited to, an anti-thrombogenic coating, which may help reduce the formation of thrombi in vivo, an antimicrobial coating, and/or a lubricating coating. The lubricating coating may be configured to reduce static friction and/kinetic friction between elongated body 12 and tissue of the patient as elongated body 12 is advanced through the vasculature of the patient. The lubricating coating can be, for example, a hydrophilic coating. In some examples, the entire working length of elongated body 12 (from distal portion 14B of hub 14 to distal end 12B) may be coated with the hydrophilic coating. In other examples, only a portion of the working length of elongated body 12 may be coated with the hydrophilic coating. This may provide a length of elongated body 12 distal to distal end 14B of hub 14 with which the clinician may grip elongated body 12, e.g., to rotate elongated body 12 or push elongated body 12 through the vasculature of the patient.

Due to the construction of elongated body 12, the thickness of the wall of elongated body 12 (measured in a direction orthogonal to longitudinal axis 16) may be relatively thin thereby providing a relatively large inner diameter ("ID" of FIG. 2) for a given outer diameter ("OD" of FIG. 2) of elongated body 12. In some examples, the thickness of the inner liner along distal liner section 18C (e.g., "$T_L$" of FIG. 2) may be about 0.0005 to about 0.003 inches (e.g., about 12.5 micrometers (μm) to about 76 μm). In some examples, the corresponding thickness of outer jacket 22 (e.g., "$T_S$" of FIG. 2) may be about 0.0015 inches to about 0.005 inches (e.g., about 38 μm to about 127 μm), such as about 0.003 inches, to create a total wall thickness of elongated body 12 within distal portion 17B (e.g., $T_L+T_S$) of about 0.003 inches to about 0.006 inches (e.g., about 76 μm to about 152 μm).

The thickness of the wall of elongated body 12 can be, for example, the thickness of inner liner 18 plus the thickness of outer jacket 22. In some examples, support element 20 may be embedded within one or both of inner liner 18 or outer jacket 22, such that a thickness of support element 20 does not contribute to the overall thickness of the wall of elongated body 12. However, in other examples, support element 20 may be only be partially embedded within one or both of inner liner 18 or outer jacket 22 or not embedded in inner liner 18 or outer jacket 22, such that a thickness of support element 20 at least partially contributes to the overall thickness of the wall of elongated body 12.

In some examples, due to the construction of elongated body 12, thickness of the wall of elongated body 12 may remain relatively thin while still providing greater flexibility within distal portion 17B and kink resistance compared to a catheter having a comparable ID/OD design and formed with a uniform liner material (e.g., a catheter constructed with only a single PTFE liner) and/or uniform outer jacket material. Additionally or alternatively, the construction of elongated body 12 with proximal and distal liner sections 18A, 18C may remain highly pushable and torqueable by the clinician compared to a catheter with distal liner section 18C extended along the entire length of elongated body 12.

In some examples, inner liner 18 may have different thicknesses. For example, proximal liner section 18A may have a thickness of about 0.001 inches (e.g., about 25 μm) and distal liner section 18C may have a thickness of about 0.001 inches to about 0.0015 inches (e.g., about 38 μm). In some examples, increasing the thickness of the liner sections 18 may increase the pushability, stiffness, and/or kink-resistance of the elongated member 12.

The inner diameter (ID) of elongated body 12 will depend on the size of vasculature and chosen size of catheter 10 to be passed through such vasculatures. In some examples, the inner diameter (ID) of catheter 10 as defined by distal liner section 18C (e.g., diameter at distal portion 17B) may be about 0.89 millimeters (mm) to about 2.24 mm. In some examples, the ID formed by distal liner section 18C may be about 2.0 mm (e.g., about 0.080 inches). In some examples, the inner diameter (ID) or elongated body 12 defined by inner liner 18 may vary along the length of elongated body 12.

In some examples, elongated body 12 may include one or more marker bands 28 that may be in the form of a full or partial ring of material more radiopaque than the material forming elongated body 12. In some examples, marker band 28 may include radiopaque materials that allow elongated body 12 (e.g., distal end 12B) to be easily observed by the clinician as catheter 10 is advanced through the vasculature of a patient. Suitable radiopaque materials may include, for example, gold, platinum/iridium alloy, palladium, or the like. In some examples, marker band 28 may be positioned over distal liner section 18C and attached to distal jacket section 22I (e.g., adhered to distal jacket section 22I or inner liner 18, or both, or embedded within distal jacket section 22I). In addition, in some examples, marker band 28 may be positioned over support element 20, such that marker band 28 is positioned between a part of support element 20 and outer jacket 22.

Elongated body 12 has a suitable working length for accessing a target tissue site within the patient from a vascular access point. In some examples the working length of elongated body 12 may be measured from hub distal end 14B of hub 14 (marked by the distal end of optional strain relief body 11) to distal end 12B of elongated body 12 along longitudinal axis 16. The working length of catheter 10 may depend on the location of the target tissue and/or the medical procedure for which catheter 10 is used. For example, if catheter 10 is a distal access catheter or other catheter used to access vasculature in a brain of a patient from a femoral artery access point at the groin of the patient, catheter 10 may have a working length of about 120 cm to about 135 cm, such as about 132 cm, although other lengths may be used. In other examples, or for other applications, the working length of elongated body 12 may have different lengths.

In some examples, elongated body 12 may define an outer diameter taper (e.g., gradient, gradation, segmented gradient or gradation, or the like) along its working length of elongated body 12. An outer diameter (OD) taper may assist with the navigability and/or maneuverability of elongated body 12 through the vasculature of a patient. In some examples, the outer diameter taper may define a continuous transition gradient from an outer diameter of elongated body 12 defined at hub distal end 14B to the outer diameter at distal end 12B of elongated body 12. In other examples, the outer diameter of elongated body 12 may define a discontinuous transition (e.g., a gradation or discrete step-downs) in outer diameter to define the outer diameter taper. The size of each discontinuous transition (e.g., each discrete step-downs) in the outer diameter may be selected to reduce the number of edges/ridges on the outer surface of elongated body 12 that may potentially catch on anatomical features within the vasculature as elongated body 12 is advanced through vasculature.

In some examples, at least a part (e.g., only part of the working length or the entire working length) of elongated body 12 may define a constant outer diameter. In such examples, support element 20 of elongated body 12 may be configured to provide sufficient support to elongated body 12 to allow the outer diameter of the elongated body 12 to remain relatively small along the length of elongated body 12 to facilitate distal flexibility about distal portion 17B while still retaining sufficient strength and pushability about proximal portion 17A. Additionally or alternatively, a relatively small outer diameter (OD) of elongated body 12 may allow for easier to navigability of the catheter 10 through tortuous vasculature of a patient. In addition, the relatively large inner diameter (ID) of the elongated body 12 may provide for more efficient and/or more effective aspiration of thrombus from the vasculature compared to catheter bodies having smaller inner diameters, e.g., due to a larger aspiration force that can be applied to the catheter, due to the larger catheter inner lumen for receiving the thrombus, or both. In addition to, or instead of, providing benefits when used to aspirate a thrombus from the vasculature, the relatively large inner diameter (ID) for a given outer diameter (OD) may accommodate a larger range of medical devices and a larger range of fluid volumes. Thus, the thin-walled elongated body 12 defining a relatively large inner diameter (ID) for a given outer diameter (OD) may be used with a larger range of medical procedures.

In some examples, by maintaining a relatively small outer diameter (OD) of elongated body 12 at distal portion 17B, which leads elongated body 12 through vasculature, elongated body 12 may better traverse through tortuous vasculature with still maintaining a relatively high level of proximal pushability due to support element 20.

In some examples, proximal portion 17A of elongated body 12 may define a relatively large outer diameter to provide better proximal support for elongated body 12, which may help increase the navigability and maneuverability of elongated body 12 through the vasculature of a patient. In some cases, proximal portion 17A may not be introduced into low profile or tortuous arteries, such that the cross-sectional size of proximal portion 17A may be increased in favor of proximal support without adversely affecting the ability of elongated body 12 to reach relatively distal tissue sites.

In some examples, the outer diameter of elongated body 12 may taper from about 6 French (e.g., 6 French or nearly 6 French) at proximal end 12A to about 5 French (e.g., 5 French or nearly 5 French) at the distal portion 17B. In other examples, the outer diameter of elongated body 12 may taper from about 4 French (e.g., 4 French or nearly 4 French) at proximal end 12A to about 5 French (e.g., 3 French or nearly 3 French) at the distal portion 17B. In other examples, the outer diameter of elongated body 12 may remain substantially constant (e.g., constant or nearly constant) in the range of about 3 French to about 6 French. In some examples, the outer diameter of elongated body 12 may be larger than 6 French, for example 8 French. The measurement term French, abbreviated Fr or F, is three times the diameter of a device as measured in millimeters (mm). Thus, an 8 French diameter is about 2.67 mm, a 6 French diameter is about 2 mm, a 5 French diameter is about 1.67 mm, a 4 French diameter is about 1.33 mm, and a 3 French diameter is about 1 mm. In some examples, the outer diameter of elongated body 12 may be about 1 mm to about 2.67 mm.

In some examples, catheter 10 may be advanced to a target location within vasculature of the patient in cooperation with a guide member (not shown) such as a guidewire, an inner catheter, both a guidewire and an inner catheter, or the like, which may aid in the navigation (e.g., steering and manipulation) of elongated body 12 through the vasculature. For example, at least part of inner lumen 24 of elongated body 12 may be configured to receive a guide member or an inner catheter, such that elongated body 12 may be guided through vasculature over the guide member or the inner catheter. In some examples, the design of distal portion 17B of elongated body 12 (e.g., the region defined by distal opening 13) may be configured to resist geometric deformation (e.g., kinking, ovalization, or the like) from forces applied to the distal tip by the guidewire or inner catheter. This resistance to geometric deformation may help improve the ease with which elongated body 12 may be guided to a relatively distal tissue site, e.g., through relatively tight turns in the vasculature and/or the responsiveness of catheter 10 as a clinician guides the distal tip of elongated body 12 through the vasculature of a patient.

In some examples, elongated body 12 may include a tie-layer (not shown) disposed between inner liner 18 and outer jacket 22 configured to help bind the two layers together. The tie-layer may include polymeric materials with good binding capabilities including, for example, thermoplastic polyurethanes such as Pellethane® 2363-80A.

Figure 3:
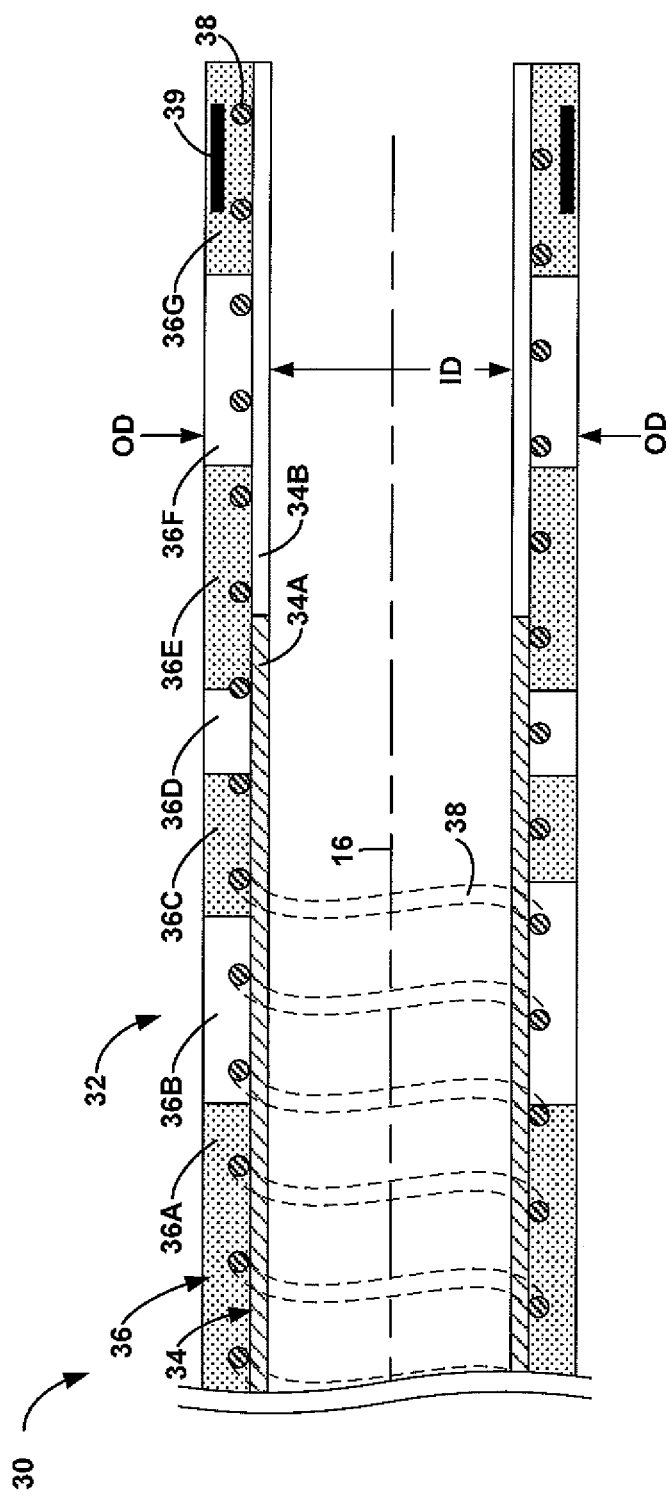
FIG. 3 is another conceptual axial cross-sectional view of a distal portion of another example catheter, which includes an elongated body and a hub.

FIG. 3 is a conceptual axial cross-sectional view of another example of a distal portion 32 of an example catheter 30 (e.g., distal portion 17B of catheter 10). The distal portion of catheter 30 includes an inner liner 34 that include a proximal liner section 34A and distal liner section 34B, a support element 38, and an outer jacket 36 that includes a proximal jacket section 36A, intermediate jacket sections 36B-36F, and a distal jacket section 36G, and a marker band 39 embedded within or located beneath distal jacket section 36G.

In some examples, support element 38 may include a support structure similar to support element 20 described above. For example, support element 38 may include a single round wire coil as shown in FIG. 3, a wire braid, or a combination of both. For example, support element 38 may include a singular wire coil comprising 0.002 inch stainless steel round wires. In other examples, support element 38 may include a flat wire braid comprising 16 0.001×0.002 inch stainless steel flat wires. In other examples, support element 38 may include a flat wire braid comprising 8 0.0005×0.002 inch stainless steel flat wires positioned over 0.0015 inch stainless steel round wire coil.

As described above, distal liner section 34B may define a lower relative hardness compared to proximal liner section 34A to provide greater flexibility within the distal portion 32 of catheter 30. In some examples, proximal liner section 34A may include PTFE and distal liner section 34B may include a thermoplastic elastomer (e.g., polyolefin elastomer ethylene butane such as Engage™ 7270) and slip agent (e.g., 5 wt. % Ampacet 100329). In some examples, distal liner section 34B may define an overall axial length of about 10 cm to about 20 cm, for example between about 16.5 cm to about 17.5 cm.

Outer jacket 36 may define a hardness gradient extending that decreases from proximal jacket section 36A to distal most intermediate jacket section 36F. In some examples, proximal jacket section 36A may include polyamides (e.g., Grilamid® TR 55) having a Shore D hardness of about 85D extending to the proximal end of the elongated body, intermediate jacket section 36B may include a polyether block amide (e.g., Pebax® 72D) having a Shore D hardness of about 72 and an axial length of about 8.2 cm, intermediate jacket section 36C may include a polyether block amide (e.g., Pebax® 63D) having a Shore D hardness of about 63 and an axial length of about 4.1 cm, intermediate jacket section 36D may include a polyether block amide (e.g., Pebax® 55D) having a Shore D hardness of about 55 and an axial length of about 6.1 cm, intermediate jacket section 36E may include a polyether block amide (e.g., Pebax® 40D) having a Shore D hardness of about 40 and an axial length of about 5.8 cm, intermediate jacket section 36F may include a polyether block amide (e.g., Pebax® 25D) having a Shore D hardness of about 25 and an axial length of about 14.9 cm, and distal jacket section 36G may include a polyolefin elastomer (e.g., Engage™ 7270) having a Shore D hardness of about 26 and axial length of about 0.2 cm.

Figure 4:
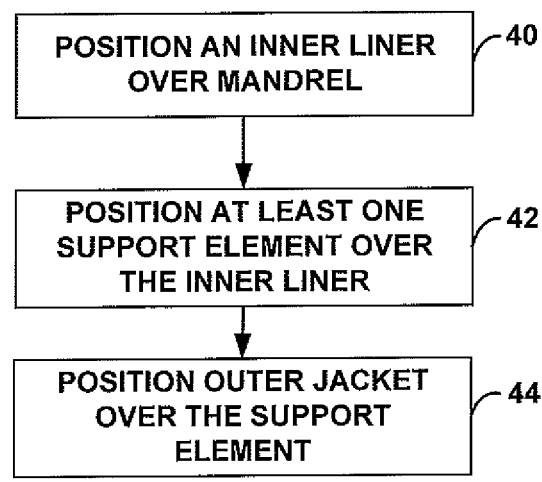
FIG. 4 is a flow diagram of an example method of forming a catheter described herein.

The catheters described herein can be formed using any suitable technique. FIG. 4 is a flow diagram of an example method of forming a catheter as described herein. The technique of FIG. 4 is described with respect to catheter 10 of FIG. 1, however the techniques may be used to form other catheters, or the catheters described herein (e.g., catheters 10, 30) may be formed using techniques other than those described in FIG. 4.

In accordance with the technique shown in FIG. 4, inner liner 18 (e.g., proximal, intermediate, and distal liner sections 18A, 18B, 18C) may be positioned over mandrel (40). The respective sections of inner liner 18 may be fabricated using any suitable technique. In some examples, the respective sections of inner liner 18 may be formed using an extrusion process in which the polymeric materials and, if applicable, slip agent, are mechanically mixed together and heated to the melting point of the underlying polymeric material and passed through a tubular extrusion process to form a tubular body having the desired thickness and diameter profiles. In some examples, the respective sections of inner liner 18 (e.g., proximal, intermediate, and distal liner sections 18A, 18B, 18B) may be positioned over a mandrel followed by being subsequently joined together (e.g., fused).

As discussed above, in some examples, elongated body 12 may taper from proximal portion 17A (FIG. 1) having a first outer diameter to distal portion 17B having a second outer diameter. In these examples, the mandrel may define a corresponding change in outer diameter and the respective sections of inner liner 18 may be approximately sized to exhibit the changes in diameter. In other examples, inner and outer diameters of elongated body 12 may remain substantially constant (e.g., constant or nearly constant). In such examples, the mandrel may define a substantially constant diameter.

In some examples, after positioning inner liner 18 over the mandrel, inner liner 18 may be heat shrunk onto the mandrel such that inner liner 18 conforms to the outer surface of the mandrel and acquire the tapered profile (if applicable) of the mandrel. In such examples, the respective sections of inner liner 18 may be sized such that the inner diameter of the respective liner sections 18 as slightly oversized to facilitate placement of the liner sections on the mandrel prior to the heat shrink process. In other examples, however, heat shrinking may not be necessary. For example, in addition to, or instead of, heat shrinking, the respective sections of inner liner 18 may be longitudinally stretched over the mandrel in order to substantially conform to the outer surface of the mandrel. In either example, inner liner 18 may define a constant inner diameter or may have different inner diameters, e.g., corresponding to the outer diameters defined by the mandrel.

After positioning inner liner 18 over a mandrel, at least one support element 20 may be positioned over inner liner 18 (42). The at least one support element may include one or more of a wire coil, wire braid, or combinations thereof. In some examples, support element 20 may include a wire braid that includes four round wires 20A (e.g., 0.001 inch round wires) woven against four flat wires 20B (e.g., 0.001× 0.002 inch flat wires), such that the respective round wires 20A are not cross woven against each other and the respective flat wires 20B are likewise not cross woven against each other. For example, the braided support element 20 is woven such that a single round wire 20A does not cross the other three round wires.

In some examples, the structural configuration of support element 20 may be at least partially defined prior to being positioned over inner liner 18. For example, a shape memory wire (e.g., NiTi alloy) or a wire of an otherwise heat-settable metal, alloy, or polymer base may be wound over a different mandrel where the wires are heat set to define at least one of the desired pitch, spacing, wind diameter, tapering profile, or length of support element 20.

After being heat set, the one or more wires of support element 20 may then be subsequently unwound from the mandrel onto a reel or a bobbin (not shown), and then re-wound/woven over inner liner 18. In some examples, defining some or all of the structural characteristics of support element 20 prior to positioning support element 20 over inner liner 18 may help control the structural characteristics of support element 20 (e.g., gap spacings, pitch, etc.), as well as control product consistency and uniformity of the support element 20 used in multiple catheters. In addition, shape-setting wires of support element 20 on a separate, heat-resistant mandrel enables the construction of the elongated body 12 using the support element 20 on a mandrel made of, for example, PTFE or other lubricious, non-heat resistant materials.

Support element 20 may be secured in place relative to inner liner 18 using any suitable technique. For example, support element 20 may be adhered to inner liner 18. In some examples, an adhesive may be positioned over inner liner 18 prior to positioning support element 20 over inner liner 18. In addition to, or instead of, an adhesive, outer jacket 22 may be used to secure support element 20 to inner liner 18. In examples in which support element 20 includes a cut hypotube, the hypotube may be defined to have a diameter less than the outer diameter of inner liner 18. As the hypotube is positioned on inner liner 18, the diameter of the hypotube may be expanded thereby creating a gap between adjacent turns of the hypotube, which may receive one or more other coil members in the created spacing.

In some examples, in addition to positioning support element 20 over inner liner 18, one or more optional marker bands 28 may be positioned over inner liner 18. In some examples, marker band 28 may be positioned over distal liner section 18C in close proximity to distal end 12B of elongated body 12 to assist with the positioning of distal end 12B within the vasculature of a patient. In addition, one or more marker bands 28 can be adhered to inner liner 18, outer jacket 22, or both inner liner 18 and outer jacket 22, or may be held in place within elongated body 12 because of being positioned between inner liner 18 and outer jacket 22.

The technique of FIG. 4 also includes positioning outer jacket 22 over support element 20 (44), including any optional marker bands 28, and inner liner 18. In some examples, the various sections of outer jacket 22 (e.g., proximal jacket section 22A, intermediate jacket sections 22B-22H, and distal jacket section 22I) may independently formed (e.g., extruded) and slid over inner liner 18 and support element 20 in the desired arrangement. The various sections of outer jacket 22 may then be heat-shrunk onto inner liner 18 and support element 20. In some examples, the heat shrinking of outer jacket 22 may help secure the respective positions of support element 20 along elongated body 12. This may help minimize the wall thickness of elongated body 12 and, therefore, increase the inner diameter of elongated body 12 for a given outer diameter by limiting the inclusion of additional layers within the wall construction of elongated body 12. In addition, the absence of additional layers (e.g., an adhesive/tie layer) that joins inner liner 18 to outer jacket 22 may contribute to an increased flexibility of catheter 10. In some examples, during the heat-shrink process, the various sections of outer jacket 22 may also be bonded (e.g., fused) together.

In some examples, the various sections of outer jacket 22 may be adhered to an outer surface of support element 20 using, for example, an adhesive/polymer that may be applied to outer surface of support element 20 prior to positioning outer jacket 22 over support element 20 and then cured after outer jacket 22 is positioned. Additionally or alternatively, the outer surface of inner liner 18 may be initially etched (e.g., chemically or mechanically roughened) to improve the bonding our inner liner 18 to outer jacket 22.

Once elongated body 12 is formed, hub 14 may be attached to proximal end 14A of elongated body 12 using any suitable technique, such as an adhesive, fusing, or any combination thereof.

In some examples, catheter 10 may be a part of an assembly that includes, e.g., a guide member. The guide member may be used to guide catheter 10 to a target tissue site within the vasculature of a patient. In some examples, a method of using catheter 10 comprises introducing a guide member or an inner catheter into vasculature (e.g., an intracranial blood vessel) of a patient via an access point (e.g., a femoral artery), and guiding elongated body 12 over the guide member. Once distal end 12B of elongated body 12 is positioned at the target tissue site, which may be proximal to thromboembolic material (e.g., a thrombus), the thromboembolic material be removed from the vasculature via elongated body 12. For example, the thromboembolic material may be aspirated from the vasculature by at least applying a vacuum force to inner lumen 24 of elongated body 12 via hub 14 (and/or proximal end 12A), which may cause the thromboembolic material to be introduced into inner lumen 24 via distal opening 13. Optionally, the vacuum or aspiration can be continued to thereby draw the thromboembolic material proximally along the inner lumen 24, all or part of the way to the proximal end 12A or hub 14.

As another example, the thromboembolic material may be removed from the vasculature using another technique, such as via an endovascular retrieval device delivered through the inner lumen 24 of the elongated body 12. In such a method the elongated body 12 can be inserted into the vasculature (for example using any technique disclosed herein) and the retrieval device advanced through the inner lumen 24 (or through another catheter, such as a microcatheter, inserted into the vasculature through the inner lumen 24) so that the device engages the thromboembolic material. The retrieval device and the material engaged thereby (together with any other catheter or microcatheter) can then be retracted into the inner lumen 24 and removed from the patient. Optionally, aspiration can be performed with or through the elongated body 12 during retraction of the retrieval device and thromboembolic material into the elongated body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

Various examples have been described. These and other examples are within the scope of the following claims.

What is claimed is:

1. A catheter comprising:
    an elongated body including proximal and distal portions, the distal portion of the elongated body comprising:
        an inner liner comprising a proximal liner section and a distal liner section comprising different chemical compositions, wherein the distal liner section has a first hardness less than a second hardness of the proximal liner section, wherein the distal liner section is less lubricious than the proximal liner section, and wherein the distal liner section extends to a distal most end of the catheter; and
        an outer jacket positioned over the inner liner.

2. The catheter of claim 1, further comprising a support element positioned between the inner liner and the outer jacket.

3. The catheter of claim 2, wherein the support element comprises a braided structure comprising at least two strands of different diameters.

4. The catheter of claim 3, wherein the braided structure comprises at least one flat or half-round wire and at least one round wire.

5. The catheter of claim 4, wherein the braided structure comprises four flat or half-round wires woven against four round wires.

6. The catheter of claim 2, wherein the support element is embedded in at least one of the inner liner or the outer jacket.

7. The catheter of claim 2, wherein the support element comprises at least one of a metal braid or a metal coil.

8. The catheter of claim 1, wherein the distal liner section comprises a thermoplastic elastomer.

9. The catheter of claim 8, wherein the distal liner section further comprises a slip agent.

10. The catheter of claim 9, wherein the slip agent comprises an amide derived from a monosaturated fatty acid and is mixed with the thermoplastic elastomer in an amount of about 0.5 weight percent (wt. %).

11. The catheter of claim 9, wherein the proximal liner section comprises a fluoropolymer.

12. The catheter of claim 1, wherein the distal liner section comprises a polyolefin elastomer and a slip agent, and the proximal liner section comprises polytetrafluoroethylene (PTFE).

13. The catheter of claim 1, wherein the proximal liner section extends to a proximal end of the elongated body.

14. The catheter of claim 1, wherein the inner liner further comprises an intermediate liner section defining a hardness less than that of the proximal liner section and greater than that of the distal liner section, the intermediate liner section being positioned between the proximal inner section and the distal liner section.

15. The catheter of claim 14, wherein the intermediate liner section comprises a polyolefin elastomer and a slip agent.

16. The catheter of claim 14, wherein the intermediate liner section and the distal liner section collectively define an axial length of at least about 0.2 cm extending along a central axis of the elongated body.

17. The catheter of claim 1, wherein the distal liner section comprises a radial thickness of about 0.0015 inches (about 38 micrometers).

18. The catheter of claim 1, wherein the distal liner section defines a lumen having a diameter of about 0.89 mm to about 2.24 mm.

19. The catheter of claim 1, further comprising a radiopaque marker band disposed over the distal liner section.

20. The catheter of claim 1, wherein the outer jacket comprises a proximal jacket section and a distal jacket section, the proximal jacket section having a greater hardness than the distal jacket section.

21. The catheter of claim 20, further comprising a plurality of intermediate jacket sections positioned between the proximal jacket section and the distal jacket section, wherein the outer jacket defines a hardness gradient of decreasing hardness moving distally from the proximal jacket section to a distal most intermediate jacket section of the plurality of intermediate jacket sections.

22. The catheter of claim 21, wherein the proximal jacket section and the plurality of intermediate jacket sections together define sequential sections of different hardnesses.

23. The catheter of claim 21, wherein the proximal jacket section defines a Shore D hardness of about 63-85.

24. The catheter of claim 21, wherein the plurality of intermediate jacket sections comprises:
   at least one jacket section comprising a polyether block amide;
   at least one jacket section comprising a polyolefin elastomer; and
   at least one jacket section comprising a polyurethane elastomer.

25. The catheter of claim 21, wherein the hardness gradient transitions from a Shore D hardness of about 72 to a Shore A hardness of about 30.

26. The catheter of claim 25, wherein the plurality of intermediate jacket sections comprises at least four intermediate jacket sections.

27. The catheter of claim 26, wherein the distal most intermediate jacket section comprises a polyurethane elastomer, and a proximal most intermediate jacket section comprises a polyether block amide.

28. The catheter of claim 21, wherein the distal jacket section defines a hardness between about a Shore A hardness of 30 and about a Shore D hardness of 55.

29. The catheter of claim 21, wherein the proximal jacket section comprises a polyamide and the distal jacket section comprises a polyolefin elastomer.

30. The catheter of claim 1, wherein the distal portion of the elongated body defines a wall thickness of less than about 0.15 mm.

31. The catheter of claim 1, further comprising a tie layer positioned between the inner liner and the outer jacket.

32. The catheter of claim 31, further comprising a support element positioned over the tie layer.

33. The catheter of claim 1, wherein the distal liner section and the outer jacket are coterminous.

34. A method for treating a thrombus within a vasculature of a patient, the method comprising:
   inserting the catheter of claim 1 into the vasculature of the patient; and
   aspirating the thrombus using the catheter.

35. A method of forming an elongated body of a catheter, the method comprising:
   positioning an inner liner over a mandrel, wherein the inner liner comprises a proximal liner section and a distal liner section comprising different chemical compositions, wherein the distal liner section has a first hardness less than a second hardness of the proximal liner section, wherein the distal liner section is less lubricious than the proximal liner section, and wherein the distal liner section extends to a distal most end of the catheter; and
   positioning an outer jacket over the inner liner.

36. The method of claim 35, further comprising forming the inner liner, wherein forming the inner liner comprises:
   extruding a mixture comprising a first polyolefin elastomer and a slip agent to form the distal liner section; and
   bonding the distal liner section to the proximal liner section to form the inner liner.

37. The method of claim 35, further comprising forming the inner liner, wherein forming the inner liner comprises:
   extruding a mixture comprising a first polyolefin elastomer and a slip agent to form the distal liner section; and
   extruding a mixture comprising a second polyolefin elastomer to form an intermediate liner section; and
   bonding a first end of the intermediate liner section to the proximal liner section and a second end of the intermediate liner section to the distal liner section to form the inner liner.

38. The method of claim 35, further comprising positioning a support element over the inner liner, wherein the support element comprises at least one of a wire braid or a wire coil.

39. The method of claim 38, wherein positioning the support element comprises weaving or wrapping a plurality of metal wires over the inner liner while the inner liner is on the mandrel, wherein the plurality of metal wires includes at least two wires of different diameters.

40. The method of claim 38, wherein positioning the support element comprises weaving four flat or half-round wires against four round wires to form the wire braid.

41. The method of claim 38, further comprising heat setting the support element on the mandrel prior to positioning the support element over the inner liner.

42. The method of claim 35, further comprising positioning a radiopaque marker over the distal liner section prior to positioning the outer jacket over the inner liner and the support element.

43. The method of claim 35, wherein positioning the outer jacket over the inner liner comprises:
   positioning a proximal jacket section over the inner liner; and
   positioning a plurality of intermediate jacket sections over the inner liner,
   wherein the outer jacket defines a hardness gradient of decreasing hardness moving distally from the proximal jacket section to a distal most intermediate jacket section of the plurality of intermediate jacket sections.

44. The method of claim 43, wherein positioning the outer jacket over the inner liner further comprises:
   positioning a distal jacket section over the inner liner, wherein the outer jacket includes a sequential arrangement of the proximal jacket section, the plurality of intermediate jacket sections, and the distal jacket section; and
   bonding contacting portions of the proximal jacket section, the plurality of intermediate jacket sections, and the distal jacket section to one another.

45. The method of claim 44, wherein the distal jacket section defines a hardness that is greater than that of the distal most intermediate jacket section.

46. A catheter comprising:
an elongated body including proximal and distal portions, the distal portion of the elongated body comprising:
an inner liner comprising a proximal liner section and a distal liner section formed from different materials, the proximal liner section comprising a fluoropolymer and the distal liner section comprising a thermoplastic elastomer, wherein the distal liner section has a first hardness less than a second hardness of the proximal liner section, wherein the distal liner section is less lubricious than the proximal liner section, and wherein the distal liner section extends to a distal most end of the catheter; and
an outer jacket positioned over the inner liner.

* * * * *